("12") United States Patent
Bertrand

(10) Patent No.: US 10,799,689 B2
(45) Date of Patent: Oct. 13, 2020

(54) METHOD AND APPARATUS FOR VALVE ADJUSTMENT

(71) Applicant: Medtronic Xomed, Inc., Jacksonville, FL (US)

(72) Inventor: W. Jeffrey Bertrand, Ventura, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 548 days.

(21) Appl. No.: 15/686,129

(22) Filed: Aug. 24, 2017

(65) Prior Publication Data
US 2019/0060621 A1    Feb. 28, 2019

(51) Int. Cl.
| A61M 27/00 | (2006.01) |
| F16K 31/524 | (2006.01) |
| F16K 15/18 | (2006.01) |
| A61B 5/03 | (2006.01) |

(52) U.S. Cl.
CPC ......... *A61M 27/006* (2013.01); *F16K 15/183* (2013.01); *F16K 31/52425* (2013.01); *A61B 5/031* (2013.01); *A61B 5/032* (2013.01)

(58) Field of Classification Search
CPC ............. F16K 31/52425; F16K 15/183; F16K 31/088; A61M 27/006
See application file for complete search history.

(56) References Cited

U.S. PATENT DOCUMENTS

| 4,595,390 A * | 6/1986 | Hakim ................. A61F 2/0036 137/530 |
| 5,643,194 A * | 7/1997 | Negre ................. A61M 27/006 137/385 |
| 6,840,917 B2 * | 1/2005 | Marion ............... A61M 27/006 137/519.5 |
| 7,771,381 B2 * | 8/2010 | McCusker .......... A61M 27/006 137/383 |
| 9,295,826 B2 | 3/2016 | Bertrand et al. |
| 2002/0022793 A1 * | 2/2002 | Bertrand ............. A61M 27/006 604/9 |
| 2005/0279960 A1 * | 12/2005 | Cabaud ............... A61M 27/006 251/304 |
| 2007/0004999 A1 * | 1/2007 | Miethke ............. A61M 27/006 604/9 |

(Continued)

FOREIGN PATENT DOCUMENTS

| EP | 1604703 A1 | 12/2005 |
| EP | 2420284 A2 | 2/2012 |
| JP | 2006014936 A | 1/2006 |

OTHER PUBLICATIONS

International Search Report and Written Opinion dated Dec. 17, 2018 in corresponding International Application No. PCT/US2018/047901.

(Continued)

*Primary Examiner* — Susan S Su
(74) *Attorney, Agent, or Firm* — Harness Dickey

(57) ABSTRACT

Disclosed is a valve assembly operable to selectively control a flow or passage of a fluid. The valve assembly may be applied to any appropriate mechanism such as a hydrocephalus shunt, fluid draining sewage system, or tank holding system. The valve assembly disclosed may include a selected profile for various applications.

19 Claims, 7 Drawing Sheets

(56) References Cited

U.S. PATENT DOCUMENTS

| | | | |
|---|---|---|---|
| 2011/0118589 A1* | 5/2011 | Negre | A61B 5/06 600/424 |
| 2012/0046595 A1 | 2/2012 | Wilson et al. | |
| 2014/0052047 A1* | 2/2014 | Wilson | A61M 27/006 604/9 |
| 2014/0336560 A1* | 11/2014 | Hakim | A61M 27/006 604/9 |
| 2015/0346732 A1* | 12/2015 | Chappel | A61M 5/16881 137/535 |
| 2016/0220794 A1* | 8/2016 | Negre | A61M 39/24 |
| 2018/0001064 A1* | 1/2018 | Pfleiderer | A61M 27/006 |
| 2018/0184943 A1* | 7/2018 | Boden, Jr. | A61B 5/062 |

OTHER PUBLICATIONS

International Preliminary Report on Patentability dated Mar. 5, 2020 in corresponding International Application No. PCT/US2018/047901.

* cited by examiner

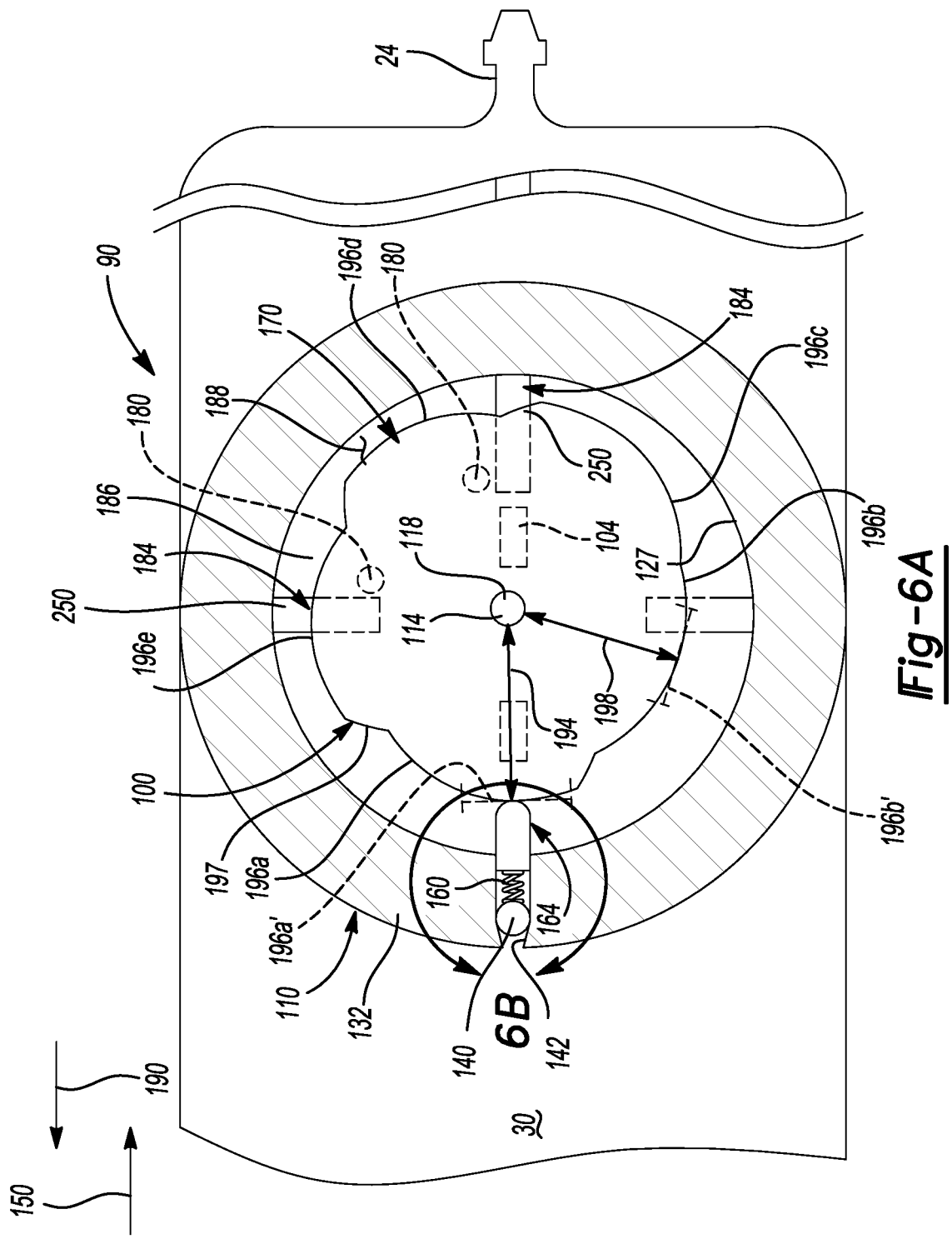

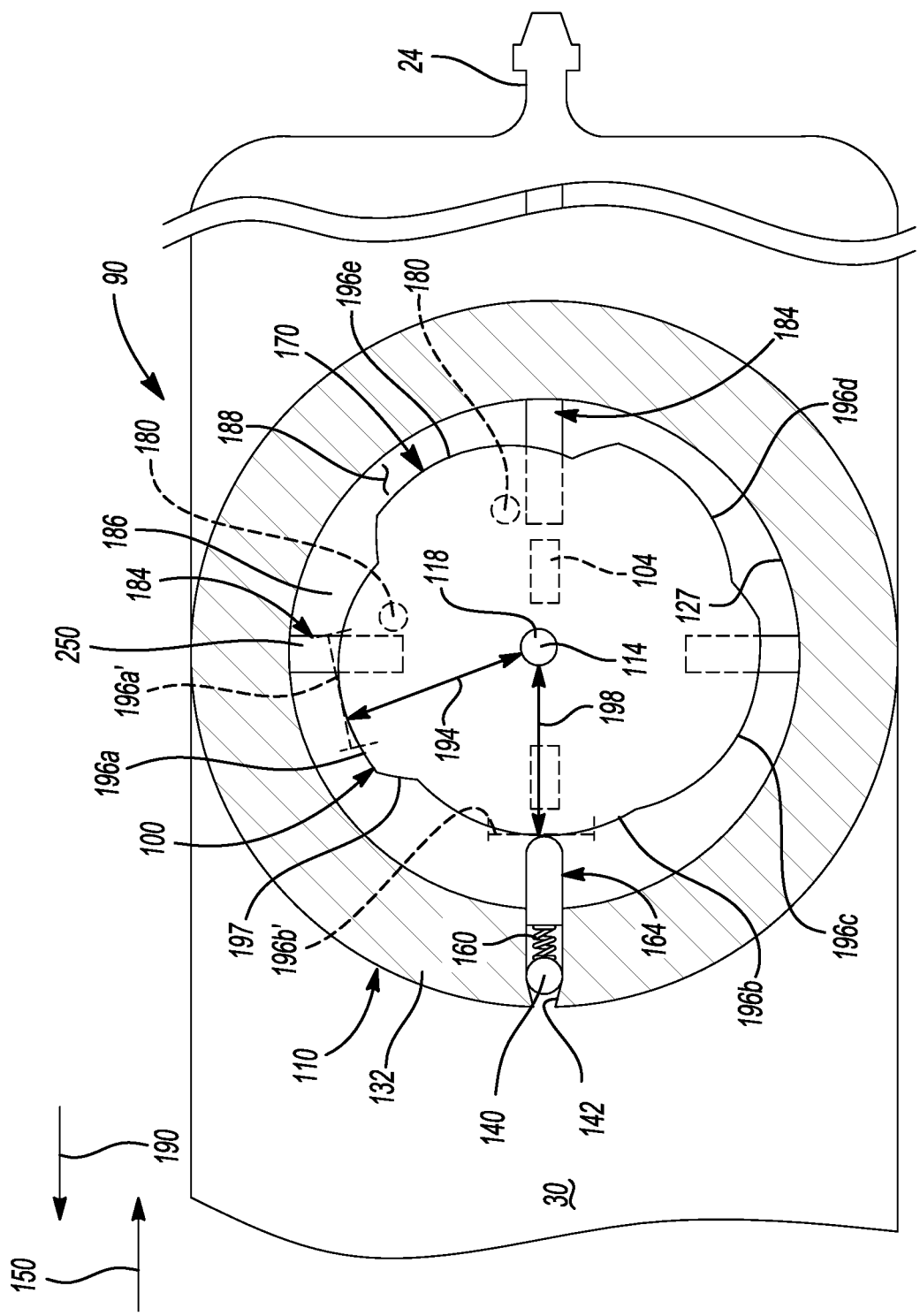

METHOD AND APPARATUS FOR VALVE ADJUSTMENT

FIELD

The present disclosure relates to an adjustment system and method, and particularly to a non-invasive adjust system and method.

BACKGROUND

This section provides background information related to the present disclosure which is not necessarily prior art.

In certain circumstances, cerebral spinal fluid (CSF) may accumulate around a brain of a subject. If the accumulation of CSF is a great enough amount, a negative impact may be felt by the subject. If negative effects are experienced or encountered by the subject, it may be selected to install a shunt and valve system to alleviate or allow the CSF to flow out of the ventricles of the brain and/or areas around the brain (e.g. between the brain tissue and the inner cranial wall) to a volume away from the cranium. Positioning and implantation of shunt systems may include positioning a catheter in the brain and a catheter away from the brain with a valve system within the catheter line. The CSF will flow through the catheter, then the valve, and then to a collecting volume. Generally known valve and shunting systems include the Codman Certas® Plus programmable valve system, sold by DePuy Synthes having a place of business in Massachusetts and the Strata® adjustable valve sold by Medtronic, Inc. having a place of business in Minnesota.

SUMMARY

This section provides a general summary of the disclosure, and is not a comprehensive disclosure of its full scope or all of its features.

A valve assembly is disclosed that may be adjusted to selectively set a resistance on a valve member (e.g. a ball or sphere) that contacts a valve seat. The greater a pressure placed on the valve member against the valve seat, the higher a force (e.g. pressure) needed to move the valve member to open the valve by moving the valve member away from the valve seat. Once the valve member is moved away from the valve seat, material may flow through the valve from a source to a distal position. In various embodiments, the valve system, therefore, includes a proximal portion at an inlet that is near a source and a distal portion at an outlet that is near or at a collection line or volume, such as a catheter.

The valve assembly includes a first member, such as moveable member or a rotor, that is moveable between positions, such as a first position and a second position, to adjust a pressure applied to a valve member. The valve member may sit in a closed position on a valve seat until a force, such as a pressure, at a force great enough to move the valve member away from the valve seat (e.g. open) and allow material, such as a fluid, to flow past the valve member. The adjustment may occur via a cam surface on the first member.

The moveable member may be substantially round and include one or more cam surfaces formed on an exterior edge of the moveable member. Each cam surface may extend or have an external surface that is at a selected distance from a center of the moveable member. Each cam surface, therefore, may include a different radius of the moveable member. The moveable member, therefore, may be moved relative to the valve member to adjust a force applied to the valve member against the valve seat.

The moveable member may rotate relative to a selected portion, such as on a projection or axle. The moveable member may further include engagement members or projections that engage fixed or stop portions of a surface of the valve assembly. Thus, the moveable member may be moved to a selected location and an interaction of the projections from the moveable member and the stop portions of the valve assembly may hold the moveable member in the selected position.

It is further understood that the present disclosure discloses and illustrates an exemplary embodiment to the use of the valve assembly in a hydrocephalus application. It is understood, however, that the valve assembly may be used to adjust the flow of a material from a first location to a second location in any appropriate application. The valve assembly, for example, may be provided to adjust or limit a flow in a mechanical application, such as in a pressure relief application (e.g. boiler) or an internal combustion engine. Alternatively, the valve assembly may be positioned in other appropriate flow control system, such as to control flow of a fluid from a commercial tank (e.g. fish tank, sewage holding tank) or other appropriate system. Therefore, it is understood, that the presently disclosed valve assembly is not required to be used in a hydrocephalus application in that such an application is merely exemplary.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6A is a top plan view of the valve mechanism of the valve assembly of FIG. 1 in a first position;

Corresponding reference numerals indicate corresponding parts throughout the several views of the drawings.

DETAILED DESCRIPTION

Example embodiments will now be described more fully with reference to the accompanying drawings.

Figure 1:
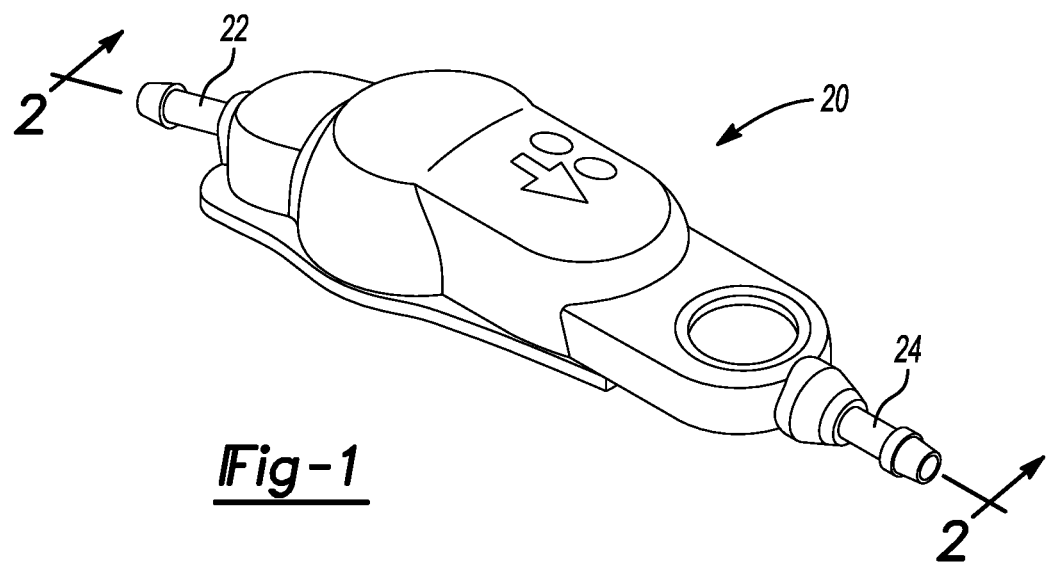
FIG. 1 is a perspective view of a valve assembly, according to various embodiments.
Figure 2:
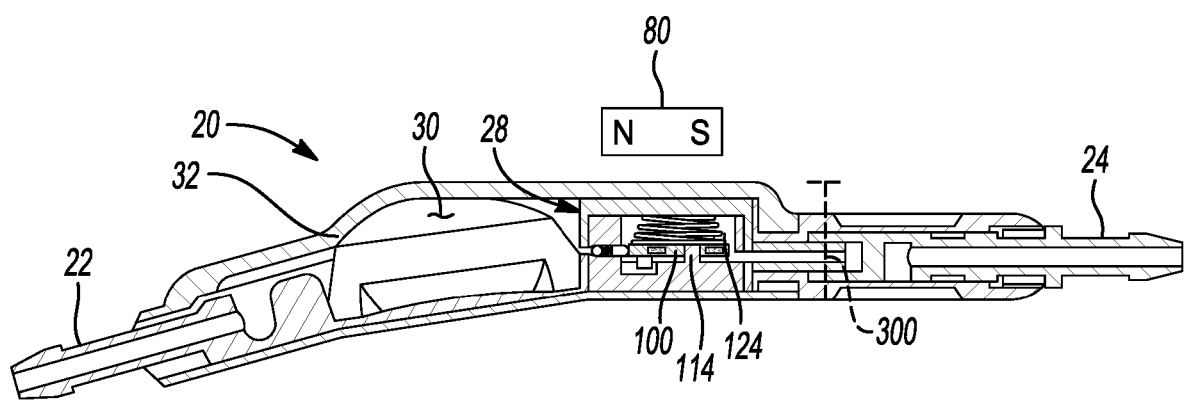
FIG. 2 is a cross-sectional view of the valve assembly of FIG. 1.
Figure 3:
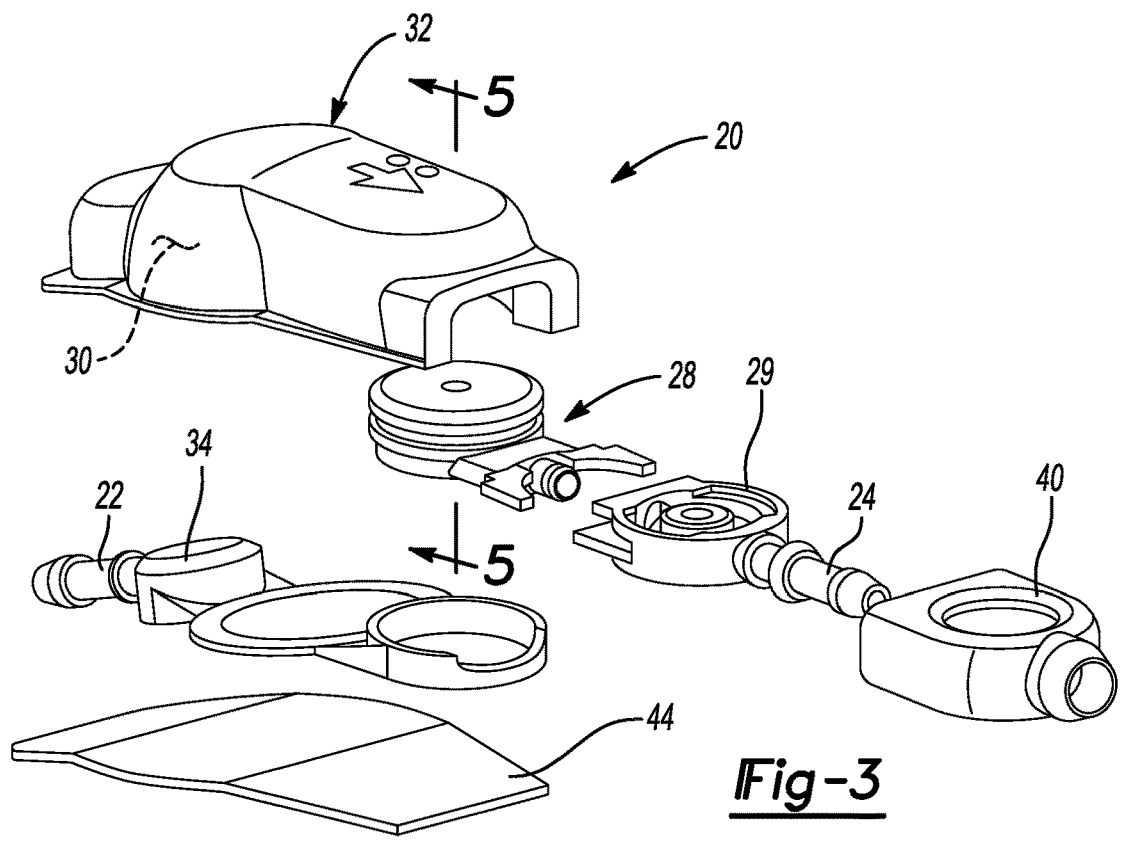
FIG. 3 is an exploded view of the valve assembly of FIG. 1.

With reference to FIG. 1, FIG. 2, and FIG. 3, a fluid control device or valve assembly 20 is illustrated. The valve assembly 20 may include an inlet connector or connection 22 and an outlet connector or connection 24. The valve assembly 20 may be positioned in various locations for selected applications. For example, as discussed herein, the valve assembly 20 may be positioned sub-dermally in a subject. For example, the valve assembly 20 may be positioned below a dermis layer of a subject and on top of a cranial bone. A conduit may be connected to respective inlet 22 and outlet 24 to drain a fluid, such as a cerebral spinal fluid (CSF), from a selected location in a brain (e.g. a ventricle) to a collection volume, such as near an abdomen of a human subject. The valve assembly 20 may include various sub-assembly portions including a cartridge assembly 28 that may incorporate various components, such as a valve mechanism 90 including a valve member 140, as discussed further herein.

The cartridge assembly 28 may connect with an outlet connector 29 that extends or includes the outlet 24. The outlet connector 29 may include various portions, such as a supplementary valve assembly, including those generally known in the art such as those disclosed in U.S. Pat. No. 9,295,826, incorporated herein by reference, and/or a supplementary or Delta® valve included in the Strata® adjustable pressure valve sold by Medtronic, Inc. having a place of business in Minnesota. The valve assembly 20 may further include a reservoir volume or region 30 that is covered by an external cover 32. The external cover 32 may further cover the cartridge 28 and an inlet connector 34 that extends to the inlet 22. As illustrated in FIG. 3, the cartridge 28 may be positioned such that reservoir volume 30 is defined at least in part by the cartridge 28 and the inlet connector 34. The cover 32 may be formed of the selected material, such as a biocompatible and flexible material including silicone. The reservoir 30, therefore, may be manipulated by pressing on the cover 32 and applying pressure to material within the reservoir 30 to cause increased flow, such as through the cartridge 28 and/or the inlet 22. An outlet cover 40 may also be provided to cover the outlet connector 29 and may be selectively sealed to the cover 32 or other appropriate portion of the valve assembly 20.

Figure 4:
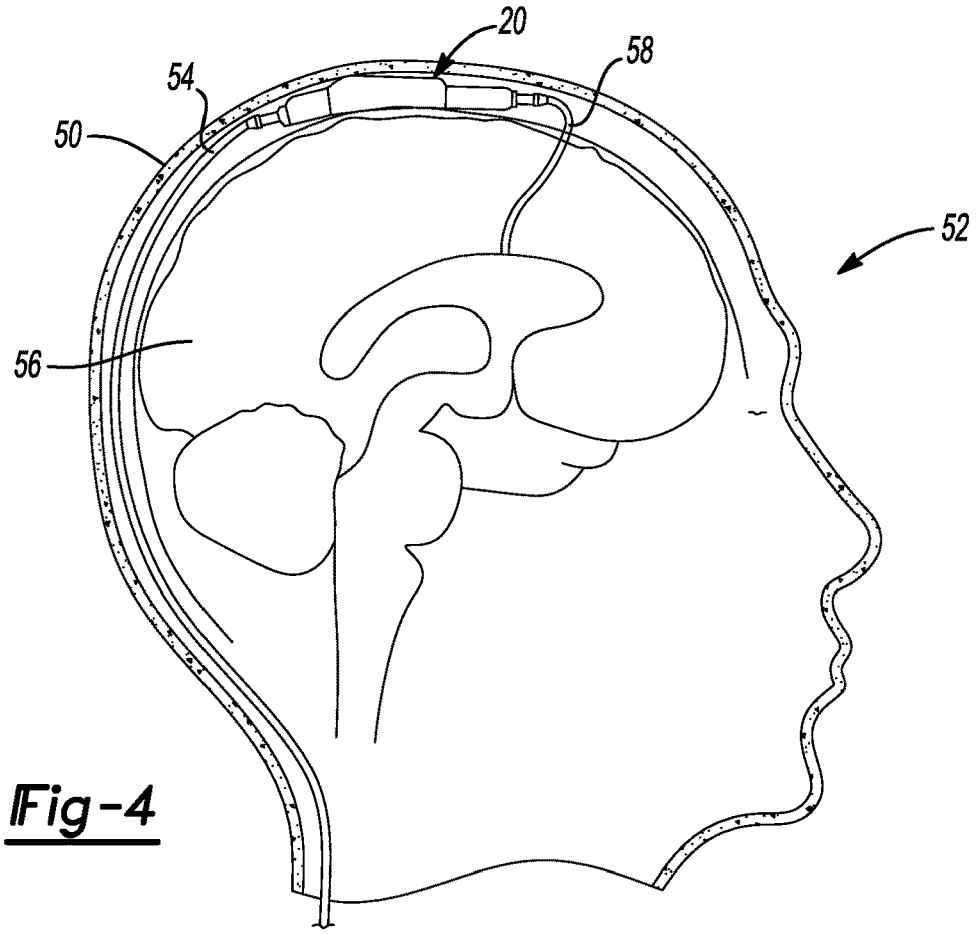
FIG. 4 is a schematic environmental view of the valve assembly of FIG. 1 in an exemplary use, according to various embodiments.

According to various embodiments, a positioning mat or base 44 may be provided to connect or position the valve assembly 20 into a selected position, such as on a boney plate of a skull of a subject 52. In various embodiments, as illustrated in FIG. 4, the valve assembly 20 is positioned below a dermis 50 of the subject 52, such as a human subject. A first catheter or tube member 54 may be positioned or implanted into a portion of a brain 56 of the subject 52. An outlet or second catheter 58 may then be directed away from the valve assembly 20 to a selected location, as discussed above, including such as an abdomen or other appropriate location.

With continued reference to FIGS. 1, 2, and 3, the valve assembly 20 may include various portions, including those discussed above, and as discussed further herein. Further, various connecting portions may be provided to interconnect various portions of the valve assembly 20 including those discussed herein, appropriate variations thereof, and other appropriate connection portions including those disclosed in U.S. Pat. No. 9,295,826, incorporated herein by reference. Nevertheless, the valve assembly 20 may include a valve portion that may be adjusted by a valve adjustment member 80 that may be used individually and/or with an adjustment assembly. The adjustment assembly may include the Strata- Varius® adjustment system and/or other adjustment tools or systems for the Strata® valve assembly, also sold by Medtronic, Inc. having a place of business in Minnesota.

The valve assembly 20 includes a valve mechanism 90 that may be included in the cartridge 28. The valve mechanism 90 may be operated to control a flow from the reservoir volume 30 through the outlet 24. Accordingly, the valve mechanism 90 of the valve assembly 20 may operate to control the flow of CSF from the brain 56 through the inlet 22 and through the outlet 24 to a selected drain location. In various embodiments, the control mechanism 80 may include a magnet having a north pole and a south pole that may interact with the valve mechanism 90 to adjust the valve mechanism 90 to control flow, as discussed herein.

Figure 5:
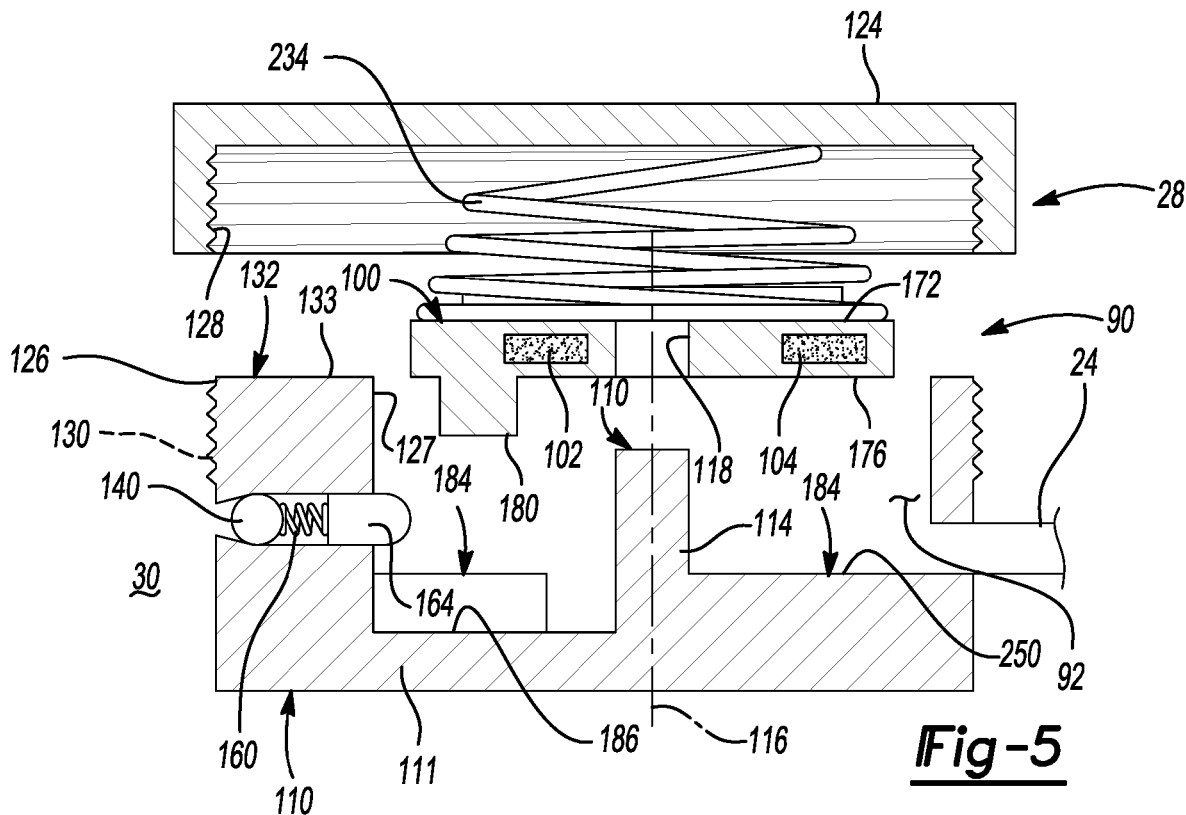
FIG. 5 is a cross-sectional view of a valve mechanism of the valve assembly of FIG. 1.

With reference to FIG. 5, the valve mechanism 90 will be discussed in greater detail. The valve mechanism 90 may be included within the cartridge 28. The cartridge 28 may include an internal volume 92. The valve mechanism 90 further includes a rotor member 100 formed of a selected material, such as a bio-compatible polymer. Incorporated into the rotor member 100, such as over molded into the rotor 100, may be one or more magnetic members 102 and 104. The magnetic members 102 and 104 may interact with the adjustor 80 to move the rotor 100 within the internal volume 92.

The valve mechanism 90, including the cartridge 28, includes a bottom cartridge member or valve cup 110 in which the rotor 100 may rotate. The bottom cartridge member 110 includes a base wall or member 111 that forms a substantially planar base surface 186. An outer or exterior cup wall 132 extends generally perpendicular to the base member 111. The outer or exterior wall 132 has an outer surface 126 that generally forms an outer dimension of the valve cup 110. The wall 132 further has an interior surface that generally forms or defines the internal volume 92 of the valve cup 110. In various embodiments, the valve cup 110 may be generally curved and the cartridge 28 (including the cap 124) may be generally cylindrical.

A central spindle or projection 114 (also referred to as an axle 114) extends from the surface 186 and generally within an interior surface 127 of the outer wall 132. The axle 114 may hold the rotor 100 and allow the rotor to rotate around the axle 114 within the cartridge bottom 110. The axle 114 extends along the axis 16 and allows the rotor 100 to rotate around the axis 116. The axle 114 may be formed in any appropriate manner such as molded with the valve cup 110, fixed to the base surface 186, or formed with the rotor 100 and positioned in a depression in the base surface 186. The axle 114 may pass through or rotatably engage a passage or throughbore 118 of the rotor 100, as illustrated in FIG. 6.

The cartridge 28 may further include the cap or cover 124 that may engage an exterior wall surface 126 of the wall 132 of the first cartridge member 110. The engagement of the cover 124 with the exterior wall surface 126 may be with any appropriate engagement mechanism. For example, the cover 124 may include an internal thread 128 that engages in external thread 130 of the wall 132. It is understood, however, that various other appropriate connection mechanisms may be provided such as an interference fit (e.g. minimal to zero tolerances between the cap 124 and the first member 110), a snap fit, welding or braising, adhesives, solvent bonding, or the like. Generally, the cap 124 engages the first cartridge member 110, such as the outer surface 126 of the wall 132 to seal a top or second side 133 of the bottom cartridge member 110 to enclose the interior volume 92 of the cartridge 28.

Figure 6B:
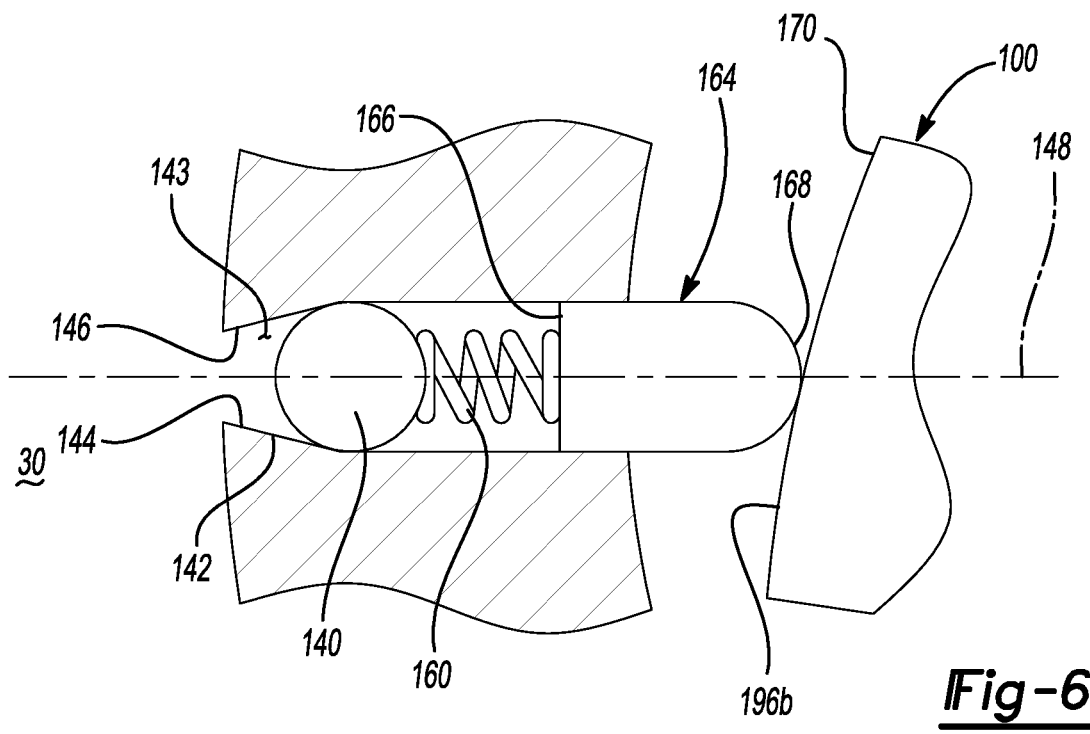
FIG. 6B is a detail view of a valve member of FIG. 6A; valve mechanism of the valve assembly of FIG. 1 in a second position.

With reference to FIGS. 6A, 6B, and 6C, the valve mechanism 90 may include a valve member 140 that is positioned relative to a valve seat 142. The valve seat 142 may be formed in a passage 143 of the wall 132. The valve seat 142, however, need not be included within a passage. The valve seat 142 may include any appropriately shaped seat, such as a conically shaped seat region. Accordingly, the valve seat 142 may include or be formed by a first wall 144. The wall 144 may angle towards the central axis 148 of the passage 143.

In operation, a fluid may flow generally in direction of arrow 150 from the reservoir 30 and out the outlet 24. In various embodiments, the fluid flowing in the direction of arrow 150 moves the valve member 140 off of the seat 142 to allow fluid to flow through the passage or channel 143 formed through the wall 132 of the first cartridge member 110. The valve member 140 may be formed as any appropriate member such as a generally spherical ball. It is understood, however, that the valve member 140 may be formed in other appropriate shapes. Further, the valve member 140 may be formed of a selected material, such as a slightly compliant material to engage the valve seat 142 in a substantially firm and sealing matter. The valve member 140, however, may also be formed of a substantially rigid or hard material (e.g. synthetic or natural ruby) such that it is not deformed when engaging the valve seat 142.

The valve member 140 is engaged by a compliant or deformably resilient member (e.g. a spring member) 160. The spring member 160 engages the valve member 140 to apply a force to the valve member 140 to seat it in the valve seat 142 to close the valve mechanism 90. The spring 160 is engaged by a follower or contact member 164. The follower 164 engages the spring 160 at a first end 166 and engages the rotor 100 at a second end 168. Accordingly, the follower 164 applies a selected pressure to the spring member 160 which, in turn, applies selected force to the valve member 140 to bias the valve member 140 in the closed, e.g. first or seated, position against the valve seat 142. The amount of force applied by the follower 164 is selected by the rotor 100 by engaging the second end 168 with a selected portion of the rotor 100. When a force, e.g. fluid pressure, is great enough from the reservoir 30 against the valve member 140, the valve member 140 is unseated from the valve seat 142. When unseated, the valve is in a second position, e.g. an open or unseated position.

With continued reference to FIGS. 6A, 6B, and 6C, the rotor 100 includes a perimeter surface 170, which may also be referred to as an external or outer edge or surface, that extends between a first or an upper surface 172 and a second or a lower surface 176 (FIG. 5), both of which may be substantially planar. It is understood that the outer edge 170 extending between the upper and lower surface 172, 176, is not intended to require a directionality of the outer edge 170 or the surfaces 172, 176, but is discussed simply for clarity of the current discussion.

Extending from the lower surface 176 (as illustrated in FIG. 5) may be one or more stop projections or legs 180. The projections 180 selectively engage one or more stop members or walls 184 that extend from a bottom or base surface 186 of the bottom cartridge member 110. Between respective stop walls 184 may be a capture area 188 that is formed as an indent or recess between the stop walls 184 within the cartridge member 110. The projection 180 from the rotor 100 engages an edge or side surface of one of the respective walls 184 to hold the rotor 100 in a select position. It is understood that more than one stop lugs or projection 180 may extend from the rotor 100 and engage one or more of the stop walls 184. Further, the stop walls extend toward a center of the axis 116 from an interior 127 of the outer wall 132.

Further, outer edge 170 of the rotor 100 includes regions, such as cam surfaces or lobes 196. Each of the cam regions 196, as discussed herein, may have different radial dimensions, relative to each other, from the central passage of 118 of the rotor 100. The number of regions 196 may be any appropriate number, and may be provided to ensure enough variability of the force applied to the follower 164 generally in the direction of arrow 190, which compresses the spring member 160 to hold the valve member 140 on the seat 142. In various embodiments, the rotor 100 may include five regions, each having selected radial dimensions. The radial dimensions may differ from each other, such as by about 0.01 millimeters (mm) to about 0.3 mm, further about 0.1 mm to about 0.2 mm, and further by about 0.12 mm. Further, the cam regions 196 having the selected radius are selected to engage the follower 164, as discussed herein. The radial dimension, as discussed herein, is further selected to engage the follower and apply a selected force to the spring 160.

For example, the rotor member 100 may include a maximum radius 194 to or at a first region or cam portion 196a and a minimum radius 198 to or at a second region 196b. As illustrated in FIGS. 6A and 6C, for example, the rotor 100, however, may include five distinct external surfaces 196a, 196b, 196c, 196d, and 196e. Each of these regions 196 may include a different radius from the central portion 118 of the rotor 100. In various embodiments, each of the regions 196a, 196b, 196c, 196d, and 196e includes a fixed radius portion. For example, the region 196b includes a fixed radius region 196b' that has a radius that is substantially equal to the radius 198 at all points in the fixed radius region 196b'. Between fixed radius regions of the cam regions, such as between the fixed radius region 196b' and a fixed radius region 196a' of the adjacent region 196a, a transition region 197 exists that may include a radius greater than the radius 194 of the fixed radius region 196b'. The stop projections 180 are positioned to engage the walls 184 at a position such that the fixed radius region of the each of the cam regions 196 engages the follower 164. Accordingly, the rotor 100 may apply a selective force against the follower 164 by positioning one of the selected surfaces 196 against the follower 164, as discussed herein.

As illustrated in FIG. 6A, the surface 196a is contacting the follower 164. The surface 196a has the radius 194 from the center passage 118 of the rotor 100. The surface 196a therefore compresses or moves the follower 164 a first distance in the direction of arrow 190 toward the spring 160 and the valve member 140 onto the seat 142. The surface 196a may be related to a specific or set amount of pressure or to an effective pressure or flow rate of the valve assembly 20 including the valve mechanism 90. The rotor 100 may be rotated around the central post 114 to engage at an alternative surface, such as the surface 196b against the follower 164.

As illustrated in FIG. 6C, the surface 196b is contacting the follower 164. The follower 164, therefore, is moved a different amount (e.g. a shorter distance) toward the spring 160. Therefore, a lower force is applied to the spring 160 and, respectively, the valve member 140 on the seat 142. Therefore, the rotor 100 may apply different amounts of force to the valve member 140 by alternating or selectively positioning a surface portion 196 against the follower 164.

Figure 6D:
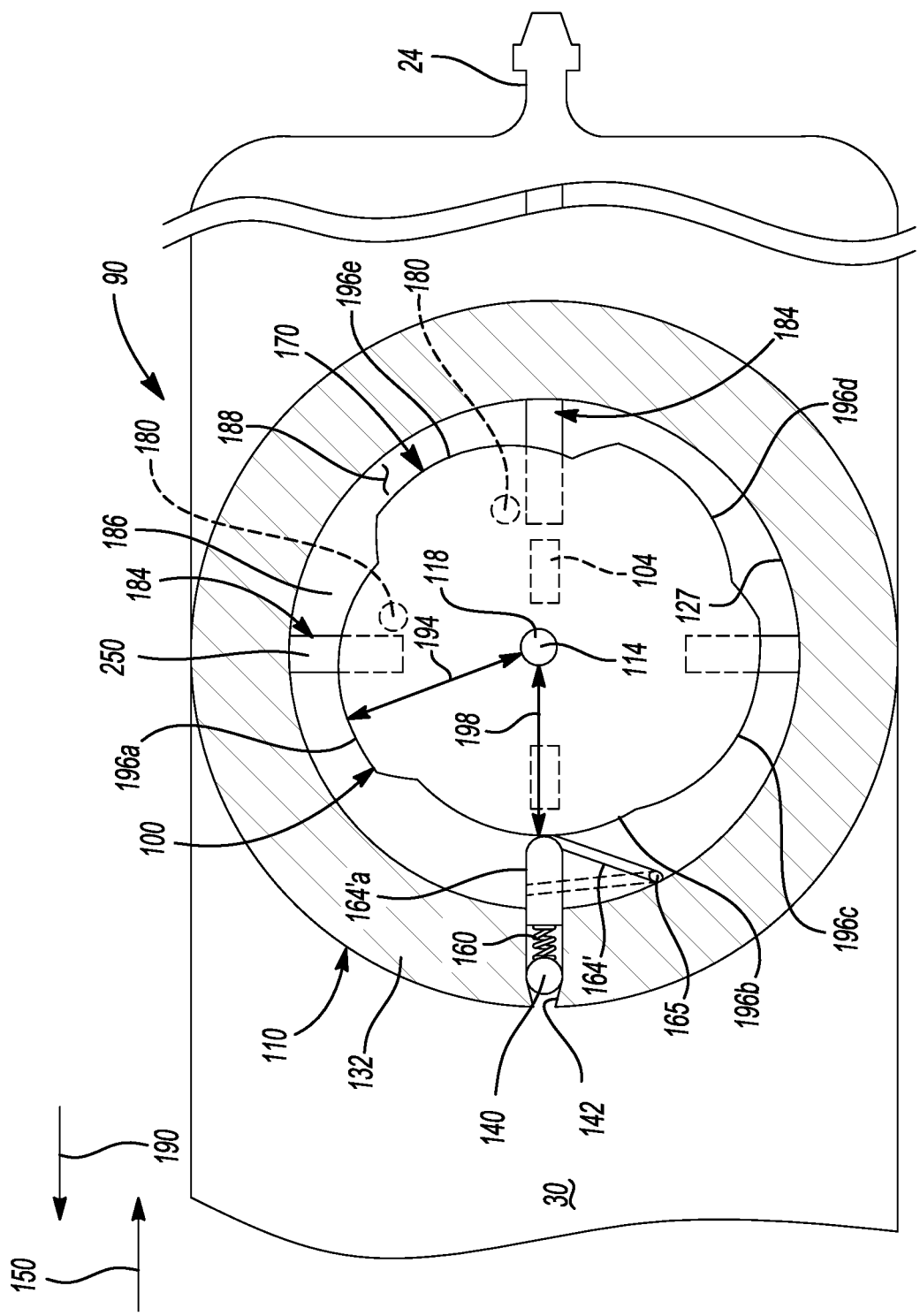
FIG. 6D is a top plan view of the valve mechanism of a valve assembly, according to various embodiments.

In various embodiments, as illustrated in FIG. 6D, a follower 164' (shown in phantom) may alternatively, or in addition to the follower 164, may be included. The follower 164' is formed as a lever or elongated member that is engaged by the rotor on the cam regions 196, similar to the follower 164. The follower 164', however, may move relative to a rotation point or region or a fulcrum 165 within the cartridge 28. Extending from the follower 164' is a spring engaging portion 164'a. The rotor 100, at one of the selected cam regions 196, engages the follower 164' to apply a force on the spring member 160 through the spring engaging member 164'a. The follower 164' may also be biased away from the spring member 160 to further regulate the force applied to the valve member 140. As a further alternative, or in addition to the follower 164 and/or 164', a second follower member 164" (shown in phantom) may also extend from the pivot point 165. In various embodiments, the cam region 196 may engage the follower 164'. The force on the follower 164' is transferred to the second follower member 164" directly or through the pivot point 165. The second follower 164" then applies the selected force to the spring 160 directly or via the follower 164'a. Thus, it is understood by one skilled in the art, that the valve mechanism 90 may include appropriate constructions to selectively apply a force to the valve member 140.

Figure 7A:
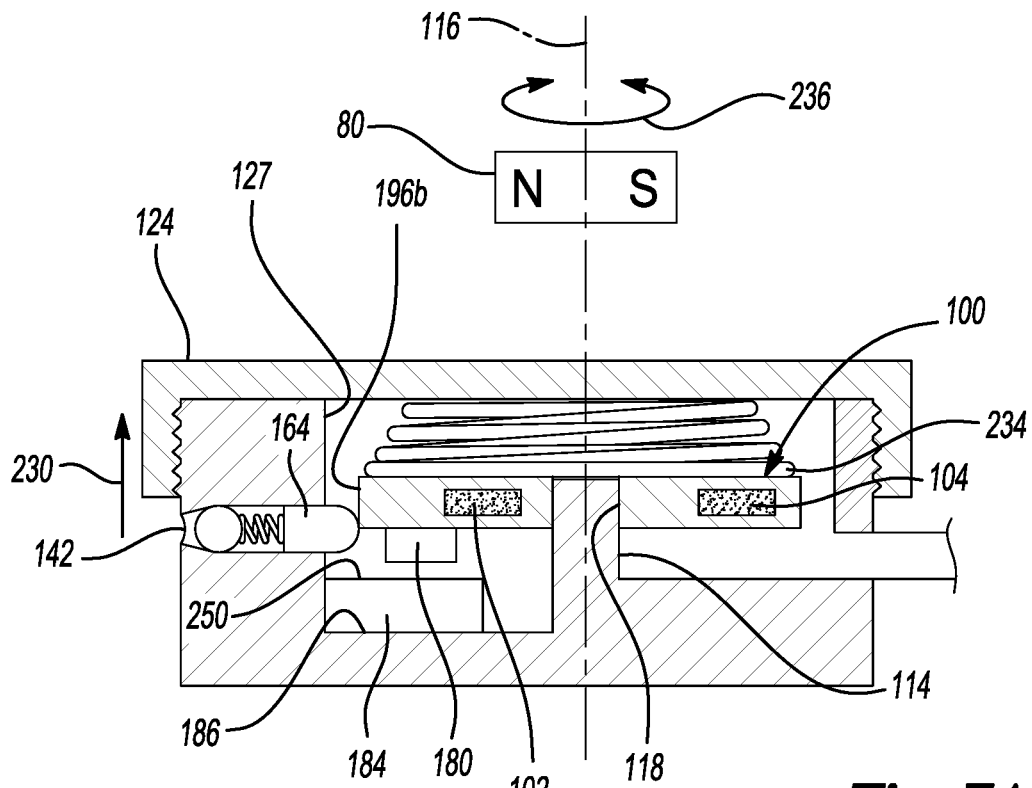
FIG. 7A is a cross-sectional view of the valve mechanism of the valve assembly of FIG. 6A in the first position.

With reference to FIG. 7A, the adjustment mechanism 80 may be any appropriate adjustment mechanism. In various embodiments, the adjustment mechanism 80 includes a magnet or other portion to interact with the rotor 100 (e.g. invasively or non-invasively) and may apply force to the magnetic members or magnetic portions 102, 104, in the rotor 100. Thus, the adjustment member 80 may be used to move or position (e.g. rotate) the rotor 100. The members 102, 104 may be fixed at a selected position to the or within the rotor 100 and interact with the adjustment tool 80.

In various embodiments, the magnetic force directs or moves the rotor 100 to lift the rotor 100 so that the stop projection 180 clears the stop wall 184, such as a top surface 250 of the stop wall 184. The rotor 100 generally moves along the central spindle 114 as it disengages the stop projection 180 from the stop wall 184. Once the stop projection 180 is disengaged from the wall 184, the rotor 100 may be rotated around the spindle or axle 114 by rotating the adjustment member 80. Therefore, the adjustment member 80 may move the rotor 100 in generally axially the direction of arrow 230 along the central axle 114. It is understood, however, that the edge 170, including the cam regions 196, may remain in contact with the follower 164 to ensure that the follower 164 does not become positioned below the rotor 100, such as between the rotor 100 and the bottom surface 186 or wall surface 250.

In the cartridge, a return spring 234 may be provided that engages the cap 124 (FIG. 7A). Therefore, the force applied to the rotor 100 is enough to overcome the spring force of the return spring 234 to allow the rotor 100 to move relative to the spindle 114 to move the lock tab 180 away from and above the locking wall 184. The adjustment member 80 may then be rotated, such as in the direction of double-headed arrow 236 to rotate the rotor 100 relative to the follower 164.

By rotating the rotor 100, a user selects which one of the cam surfaces 196 is to engage the follower 164 and apply a force to the valve member 140. Thus, the tool 80 allows the user to select a force applied to the valve member 140 by allowing the user to rotate the rotor 100 around the axle 114. Once the selected cam region 196 is positioned against the follower 164, the adjustment member 80 may be moved away from the rotor 100 to allow the return spring 234 to bias the rotor 100 against the bottom surface 186 of the first member 110. The rotor 100, therefore, is allowed to move toward the bottom surface 186 when the tool 80 is removed such as the magnetic force no longer effects the members 102, 104.

Figure 7B:
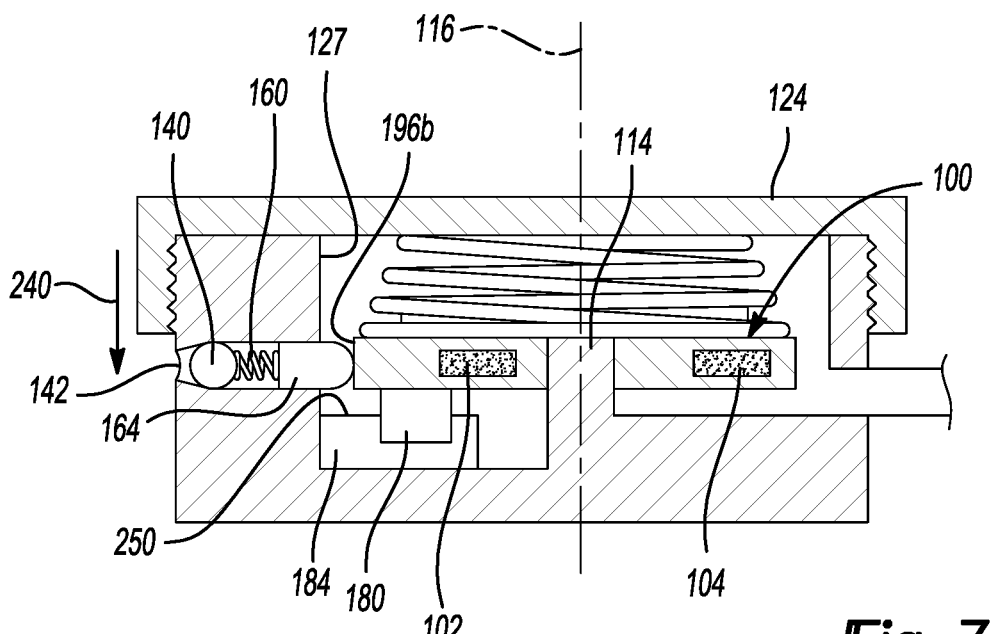
FIG. 7B is a cross-sectional view of the valve mechanism of the valve assembly of FIG. 6C in the first position.

With reference to FIG. 7B, removal of the adjustment device 80 causes the rotor 100 to move generally in the direction of arrow 240 on the spindle 114. The stop member 180 then is positioned below the surface 250 of the wall 184 and engages the wall 184 to hold the rotor 100 in a selected position. The selected surface, such as the surface 196b that engages the follower 164 then compresses the spring 160 a selected amount to engage the valve member 140 into the seat 142.

Accordingly, the engagement of the valve member 140 into the valve seat 142 is accomplished via a force that is substantially from a side or edge of the rotor 100. Therefore, the motion or direction of force provided by the rotor 100 is substantially lateral, such as in a direction that is substantially perpendicular to the axis of rotation 116, which may be defined by and extend through the axle 114.

In various embodiments, the positioning of the stop projection 180 relative to the wall 184 does not substantially affect the force applied to the follower 164. For example, the wall 184 includes the top surface 250. When the stop portion 180 is on the top surface 250 of the wall 184, the cam surface 196b applies substantially the same force to follower 164 as if the stop portion 180 is within the indent or depression 188 between respective stop walls 184. Accordingly, the force of the valve mechanism 90 is not substantially altered based upon a position of the stop member 180 in a direction along the axis 116. Rather the force is applied by the outer surface 196b onto the follower 164 to apply the force to the valve member 140.

Further, the valve mechanism 90, including the entire valve assembly 20, may be formed of selected materials. For example, the rotor 100 and the cartridge 28 may be formed of appropriate biocompatible polymers including high molecular weight polyethylene, thermoplastic polymers including polysulfone, or other appropriate polymers. Accordingly the valve mechanism 90 may be substantially self-lubricating so as to not bind or apply other forces to the valve mechanism 90. Also, as discussed above, the cover 32 of the valve assembly 20 may be formed of a soft or pliable material, such as a silicone to allow adjustment of the valve assembly 20.

Returning reference to FIG. 2, the valve assembly 20 may have a maximum height 300 that is about 2 millimeters (mm) to about 12 mm, including about 4 mm to about 12 mm, and further including about 5 mm to about 8 mm. The maximum height 300 may, when positioned on the subject 52 as illustrated in FIG. 4, provide a low or slight obstruction to the dermal surface 50 of the subject 52. The height 300, therefore, may be selected or appreciated by the subject 52 to have a selected projection.

The position of the rotor 100 in the cartridge 28 to engage the follower 164 at an edge of the rotor 100 may allow for efficient and known selected force to be applied to the follower 164. The position of the rotor stop 180 relative to the wall 184 does not substantially effect the force applied to the follower 164 during operation of the valve assembly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A valve assembly to control a flow of a fluid through a valve mechanism, comprising:
    an inlet having an opening to allow the fluid to pass;
    the valve mechanism including:
        a valve cup having an outer wall extending from a base wall;
        a first stop wall extending from a base surface of the base wall and interior to an internal surface of the outer wall;
        an axle extending from the base surface;
        a rotor having (i) a throughbore configured to pass over the axle and allow the rotor to rotate relative to the base surface and (ii) an outer surface having at least (a) a first region and (b) a second region, wherein the first region has a first radius and the second region has a second radius different from the first radius;
        a valve member;
        a valve biasing assembly having a first portion and a second portion;
        a valve seat formed in a passage through the outer wall;
        wherein the valve member is positioned at the valve seat and biased into a closed position with the valve biasing assembly,
        wherein the valve biasing assembly is engaged by the exterior surface of the rotor to apply a selected force to the valve member;
        wherein the valve biasing assembly includes at least a spring member and a follower;
        wherein the valve member, the spring member, and the follower are at least partially received within the passage; and
    an outlet to allow the fluid to flow away from the valve mechanism.

2. The assembly of claim 1, further comprising:
    a reservoir enclosing a volume between the inlet and the valve mechanism.

3. The assembly of claim 1, wherein the axle is spaced away from the first stop wall.

4. The assembly of claim 1, wherein
    the follower member extends along an axis from a first end to a second end,
    wherein the valve member is biased into the closed position with the spring member and the follower member,
    wherein the first end of the follower member is engaged by the exterior surface of the rotor to apply a selected force on the spring member with the second end.

5. The assembly of claim 1, wherein the follower member is a lever follower member;
    wherein the valve member is biased into the closed position with the spring member and the layer follower member,
    wherein the lever follower member is engaged by the exterior surface of the rotor to apply a selected force on the spring member.

6. The assembly of claim 5, wherein the lever follower member is moveable around a fulcrum when engaged by the exterior surface of the rotor.

7. The assembly of claim 1, wherein the base surface is substantially planar.

8. The assembly of claim 1, further comprising:
    a magnetic member fixed to the rotor;
    wherein the magnetic member is configured to interact with an adjustment tool to raise the rotor and rotate the rotor around the axle.

9. The assembly of claim 1, wherein the rotor further includes:
    a substantially planar surface;
    a projection extending from the substantially planar surface;
    wherein the projection selectively engages either a top surface or a side surface of the first stop wall to hold the rotor in a selected axial and rotational position.

10. The assembly of claim 1, further comprising:
    a return spring positioned to engage and bias the rotor toward the base surface.

11. A valve assembly to control a flow of a fluid, comprising:
    a valve cup having:
        a substantially planar base surface;
        an external wall extending from the substantially planar base surface;
        a first stop wall extending from the substantially planar base surface;
        an axle extending from the substantially planar base surface;
    a rotor having:
        a first substantially planar surface opposed to a second substantially planar surface;
        a throughbore extending through both the first substantially planar surface and the second substantially planar surface, wherein the axle is configured to pass through the throughbore;
        an outer surface having at least (a) a first cam region and (b) a second cam region, wherein the first cam region has a first radius and the second cam region has a second radius different from the first radius;
    a magnetic member;
    a valve seat formed in a passage through the external wall of the valve cup;
    a valve member configured to engage the valve seat to seal the passage;
    a valve biasing assembly having a first portion and a second portion; and
    a cap to engage the valve cup and seal an internal portion of the valve cup;
    wherein the valve member is positioned at the valve seat and biased into a closed position with the valve biasing assembly,
    wherein the valve biasing assembly is engaged by the outer surface of the rotor to apply a selected force to the valve member,
    wherein the valve biasing assembly includes at least a spring member and a follower, wherein the valve member, the spring member, and the follower are at least partially received within the passage.

12. The valve assembly of claim 11, wherein the first radius is different from the second radius by about 0.1 mm to about 0.2 mm.

13. The valve assembly of claim 11, wherein the follower extends from the passage along an axis from a first end to a second end to be selectively engaged by the exterior outer surface of the rotor with the first end.

14. The valve assembly of claim 11, further comprising:
a pliable cover;
wherein the pliable cover defines at least in part a reservoir relative to the external wall.

15. A method to operate a valve assembly to control a flow of a fluid through a valve mechanism, comprising:
positioning the valve assembly configured to be connected to an inlet and an outlet to allow the fluid to flow to and away from the valve mechanism;
overcoming a return spring force of a return spring to disengage a rotor projection from a stop wall;
positioning a rotor at a first position relative to a valve member by rotating the rotor around an axle that extends from a base surface of a valve cup, wherein in the first position a first cam surface of the rotor engages the valve member;
wherein the cam surface is formed on an exterior surface of the rotor and the first cam surface defines a first radius;
axially moving a follower member along an axis to axially move the valve member along the axis upon rotating the rotor.

16. The method of claim 15, wherein engaging the rotor includes positioning an adjustment member to magnetically interact with at least a portion of the rotor.

17. The method of claim 16, wherein engaging the rotor further includes lifting the rotor relative to the base to disengage a stop projection extending from the rotor from a stop wall.

18. The method of claim 17, further comprising:
rotating the rotor to a second position relative to the valve member by rotating the rotor around the axle that extends from the base surface of the valve cup, wherein in the second position a second cam surface of the rotor engages the valve member;
wherein the second cam surface has a second radius different than the first radius.

19. The method of claim 15, further comprising:
implanting the valve assembly in line with a conduit.

* * * * *